US00PP23179P2

(12) United States Plant Patent
Korlipara

(10) Patent No.: US PP23,179 P2
(45) Date of Patent: Nov. 13, 2012

(54) ***GEUM* PLANT NAMED 'FIRE STORM'**

(50) Latin Name: ***Geum* hybrid**
Varietal Denomination: Fire Storm

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/200,291

(22) Filed: Sep. 21, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — Klarquist Sparkman, LLP

(57) ABSTRACT

A new and distinct *Geum* plant named 'Fire Storm' characterized by orange flower color, large, double flowers, a compact, upright habit, long bloom time, and excellent vigor.

1 Drawing Sheet

Botanical designation: *Geum* hybrid.
Variety denomination: 'Fire Storm'.

BACKGROUND OF THE INVENTION

The present invention relates to a new and distinct cultivar of *Geum* plant given the name 'Fire Storm'. *Geum* is in the family *Rosaceae*. The new cultivar is a whole plant mutation found in a cultivated area, more specifically, a greenhouse in Canby, Oreg.

Compared to *Geum* 'Fireball' (unpatented), the new cultivar is much more compact. Both are sterile and do not produce seeds.

Compared to *Geum* 'Totally Tangerine' (U.S. Plant Pat. No. 22,041), the new cultivar has double flowers rather than single.

SUMMARY OF THE INVENTION

The following traits have been repeatedly observed and are determined to be the unique characteristics of 'Fire Storm'. These characteristics in combination distinguish 'Fire Storm' as a new and distinct cultivar:

1. orange flower color,
2. large, double flowers,
3. compact, upright habit,
4. long bloom time, and
5. and excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 1 and a half year old *Geum* 'Fire Storm' growing in a two gallon container outside in full sun in May in Canby, Oreg.

DETAILED PLANT DESCRIPTION

The following is a detailed description of the new *Geum* cultivar based on observations of a 1 and a half year old specimen grown in a two gallon container in full sun under typical outdoor conditions in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Type*.—Herbaceous perennial.
*Hardiness*.—USDA Zone 5-9.
*Size*.—42 cm wide and 18 cm tall to top of the foliage.
*Form*.—Mound.
*Vigor*.—Excellent.
*Number of rosettes*.—About 15.

Stem: None.

Leaf:

*Type*.—Simple, rosulate and cauline.
*Arrangement*.—Rosette and alternate.
*Surface texture*.—Pubescent on both sides.
*Venation*.—Pinnate and impressed.
*Petiole*.—Clasping, pubescent, Yellow Green 146B.
*Rosulate leaves*.—Lyrate, grow to 15.5 cm long and 4.5 cm wide, 7 to 9 foliate, margins serrate, tips acute, bases attenuate; terminal leaflet rhomboid, grows to 3.5 cm long and 3 cm wide, shallowly cut 3 to 6 times.
*Cauline leaves*.—Lyrate, sessile, grow to 6 cm long and 3 cm wide, 3 to 5 foliate, stipulate, leaflets obovate, irregularly lobed and incised, tips acute, bases attenuate; stipules foliar, grow to 21 mm long and 12 mm wide, irregularly incised, Yellow Green 146B.
*Color*.—Topside Green 137A including veins, bottom side Yellow Green 146B with veins 146C.

Inflorescence:

*Description*.—In cymes from each rosette of 2 to 5 flowers.

*Size of inflorescence*.—Grows to 6 cm wide and 3.5 mm deep.

*Peduncle*.—Grows to 34 cm tall and 3 mm wide, pubescent, Yellow Green 146C tinted Greyed Purple 187B at base on near top where exposed to sun.

*Pedicel*.—2 cm long and 1.8 mm wide, Yellow Green 146C tinted Greyed Purple 187B at base on near top where exposed to sun.

Flower bud:

*Size*.—10 mm long and 12 mm wide.

*Shape*.—Bowl shaped overall.

*Surface*.—Pubescent on calyx, glabrous on petals.

*Color*.—Yellow Orange 22B with Orange Red N34A on veins and tips.

Flower:

*Type*.—Actinomorphic, double.

*Size*.—45 mm wide and 20 mm deep.

*Corolla description*.—20 to 22 petals, each orbicular to broadly ovate in shape and notched one to four times on top, grows to 20 mm long and 17 mm wide, margins entire to slightly undulate, tip obtuse to notched, base obtuse, glabrous on both sides, top side Orange 25A with edges sometimes Orange Red N34A, bottom side Yellow-Orange 22B with Orange Red N34A on veins and tips where exposed.

*Calyx description*.—5 sepal lobes, campanulate, 5 mm deep and 10 mm wide, Yellow Green 146A on top and bottom sides and pubescent outside and inside, lobes ovate, reflexed and flattened to tube, margins entire, tips acuminate, each lobe 5 mm long and 3 mm wide.

*Pistil description*.—1 in number, 5 mm long and 5 wide, ovary 5 mm long and 5 mm wide, Yellow Green 146C and covered with long white hairs, about 130 styles and stigmas, styles 4 mm long, Yellow Orange 21C; stigmas Greyed Purple 187A.

*Stamen description*.—About 160, 7.5 mm long, filaments 7 mm long, Yellow Orange 23A, anthers 0.5 mm long, Greyed Purple 187A, pollen none.

*Fragrance*.—None.

*Lastingness*.—Each flower last approximately one week in summer and up to two weeks in cool weather.

*Bloom time*.—April to June with sporadic rebloom through September.

Fruit: None.

Seed: None, sterile.

Disease and pests: The new cultivar is typical to the genus. No known resistances to pests or diseases. No problems have been observed in Canby, Oreg.

I claim:

1. A new and distinct *Geum* plant as herein illustrated and described.

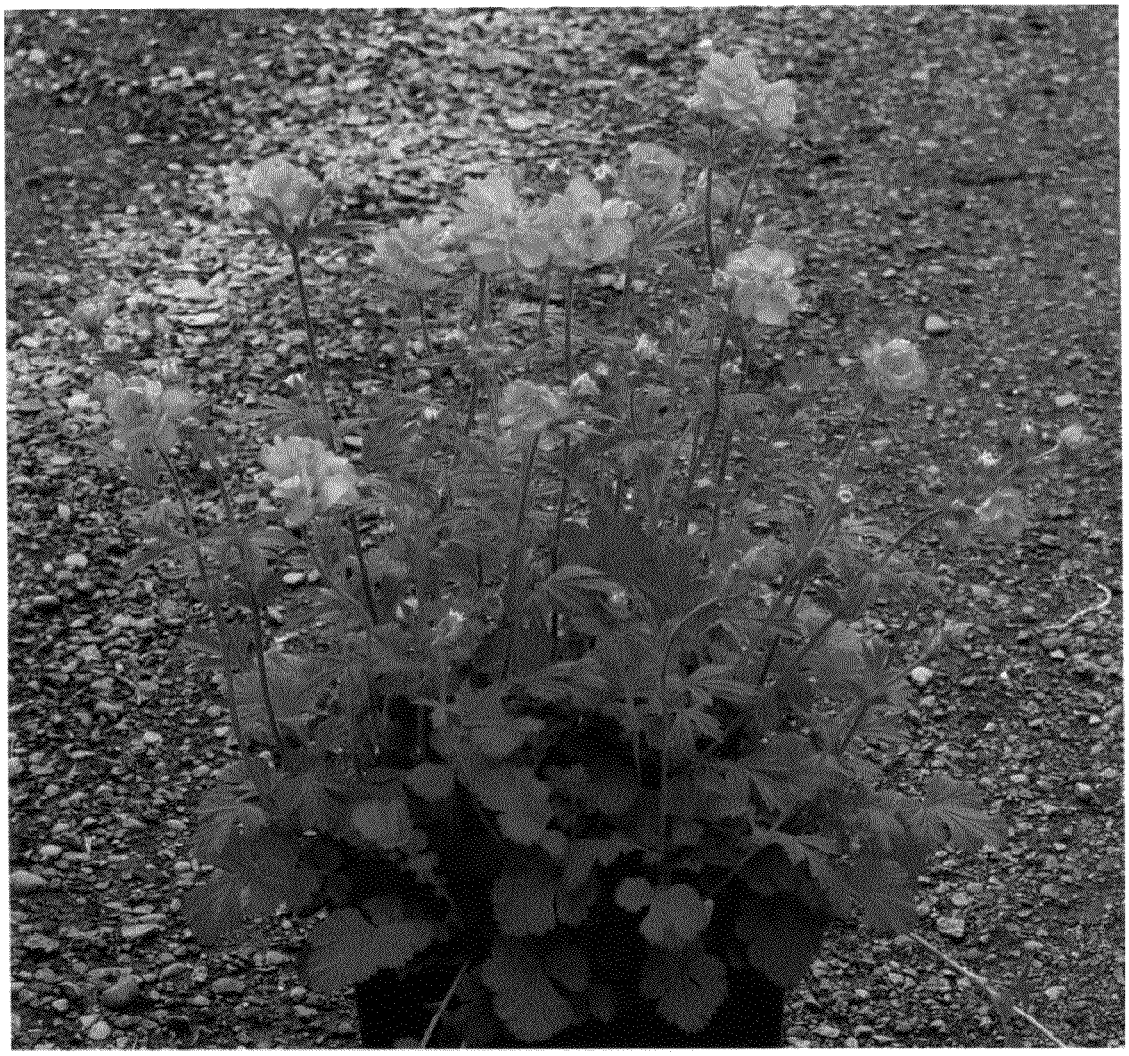

* * * * *